United States Patent [19]

Gourlandt et al.

[11] 3,964,481

[45] June 22, 1976

[54] AUTOMATIC INJECTION DEVICE

[76] Inventors: Albert Joseph Gourlandt; Georges Charles Gourlandt, both of Les Gresillons, 78750 Gambais; Yves Bernard Cauquelin, 1, Square Montmorency, Residence Auteuil, 78150 Le Chesnay Parly 2; Jean Francois Lafon, Moulin de Fourcon, Saint-Germain-les-Arpajon, 91290 Arpajon, all of France

[22] Filed: Sept. 23, 1974

[21] Appl. No.: 508,447

Related U.S. Application Data

[63] Continuation-in-part of Ser. No. 349,979, April 11, 1973, abandoned.

[30] Foreign Application Priority Data

| | | |
|---|---|---|
| Apr. 28, 1972 | France | 72.15380 |
| July 3, 1974 | France | 74.23153 |

[52] U.S. Cl. ........................ 128/218 A; 128/DIG. 1

[51] Int. Cl.² ........................ A61M 5/00

[58] Field of Search ........... 128/215, 218 R, 218 A, 128/218 F, 218 C, 218 P, 218 PA, 218 D, 305, 253, 303.1, DIG. 1, 318; 141/258, 284, 329; 222/80, 82–83

[56] References Cited

UNITED STATES PATENTS

| | | | |
|---|---|---|---|
| 2,531,267 | 11/1950 | Harnisch | 128/218 F |
| 2,761,450 | 9/1956 | Sandy | 128/318 |
| 2,952,257 | 9/1960 | Rubery | 128/253 |
| 3,217,445 | 11/1965 | Wade | 128/218 R |
| 3,302,645 | 2/1967 | Lockmiller | 128/253 X |
| 3,362,406 | 1/1968 | Logsdon | 128/218 R |
| 3,494,358 | 2/1970 | Fehlis et al. | 128/218 R |
| 3,641,998 | 2/1972 | Lyon et al. | 128/218 A |
| 3,674,009 | 7/1972 | Williamson | 128/218 A |
| 3,720,211 | 3/1973 | Kyrias | 128/215 |
| 3,841,328 | 10/1974 | Jenson | 128/218 A |

FOREIGN PATENTS OR APPLICATIONS

| | | | |
|---|---|---|---|
| 519,151 | 12/1955 | Canada | 128/218 F |
| 519,683 | 12/1955 | Canada | 128/218 F |

*Primary Examiner*—John D. Yasko

[57] ABSTRACT

The automatic injection device of the invention comprises an injection syringe having a syringe body provided with a lateral injection-liquid supply tubulure, retention means for retaining the animal to be treated, enabling the latter to be placed in a given transverse position and at a given angle with respect to the syringe, syringe displacement means for advancing and withdrawing the syringe at each injection, and piston displacement means for displacing the piston with respect to the syringe body. Such a device enables for example about at least 2000 chicks to be vaccinated per hour, while at the same time ensuring a dosing accuracy on the order of 1/100 and an exact location of the point of injection.

16 Claims, 8 Drawing Figures

AUTOMATIC INJECTION DEVICE

This application is a continuation in-part application of copending application Ser. No. 349,979, filed on Apr. 11, 1973 now abandoned.

The present invention has for its object an automatic device for injecting a treatment liquid by means of a syringe, for example a medicine or a vaccine, into an animal. The invention also relates to an accurate dosing syringe which is advantageously usuable as a constituent syringe in the said device.

The problem has arisen of treating, in particular vaccinating, animals at a high rate, especially in stock farms comprising a great number of individuals, i.e. in the first place, in farms where small animals are bred, as is the case, for example, in aviculture. As an example, one-day old chicks are vaccinated by the specialists in avicultural reproduction before being sold to stockbreeders, this vaccination being necessary to avoid the extension of epidemics and to ensure a maximum rate of survival of the chicks. It is readily understood that, owing to the high cost of the vaccines and to the maximum chick purchase price which is acceptable to the purchasers, it is necessary to be able to vaccinate the chicks at a high rate and efficiently, i.e. by locating in the best possible way the point and the depth of injection and by introducing exactly the required quantity of vaccine; indeed, the introduction of too small a dose will not ensure a satisfactory immunity, whereas the injection of too high a dose will result in excessive consumption of vaccine. More generally, it is of interest, whatever the nature of the animal and of the injected substance, to obtain a high vaccination rate as well as a high accuracy with regard to the volume of the injected dose and the location of the point of injection and the injection depth. Moreover, it is useful to be able to modify at will the position of the point of injection on the animal, as well as the injection depth.

The existing injection devices to not enable such requirements to be met in any way. Indeed, where use is made of a conventional, manually or semi-automatically actuated syringe, even associated with a device for automatic filling of its container with injection liquid, the injection rate remains relatively low and the injection of the treatment liquid into the animal never takes place under the same conditions for all the individuals, owing, in particular, to the difficulty of positioning the point of injection (especially in the case of small animals) as a result of the reduced attentiveness of the operator due to his tiredness. Furthermore, owing to the dosing in the syringes used nowadays being adjustable by adjusting the travel of the syringe piston, it is very difficult to predetermine the dose to be injected at the desired value with an accuracy higher than ± 5% and to check a possible disadjustment of the dosing during operation.

The injection device of the present invention enables these various drawbacks to be remedied and ensures an accurate and predetermined positioning of the animal with respect to the syringe, a high dosing accuracy, a high rate of vaccination and a great number of adjustment possibilities.

BRIEF SUMMARY OF THE INVENTION

The injection device according to the invention comprises:

— an injection syringe provided with a lateral injection-liquid supply tubulure;

— retention means for retaining the animal to be treated, enabling the latter or the treated part thereof to be placed in a given transverse position and at a given angle with respect to the syringe;

— means for advancing and withdrawing, at each injection, the syringe relative to the said retention means; and — means of displacement of the piston with respect to the syringe body.

The aforesaid retention means preferably include a retention plate and at least one stop member provided on said plate, said stop member being either integral with said plate or rigidly secured on its external surface and comprising usually two abutment faces intersecting so as to form a concave or convex abutment corner at the level of which may be located an articulation of a member or limb of the animal, with the two animal parts connected by said articulation extending along each said face of said stop member.

The said retention plate is passed through by a hole enabling the syringe needle end to project outwardly of the external surface of the retention plate, when the syringe is in its advanced position and to be retracted inwardly of said surface when said needle end is in its rearward position, said aperture being located in the immediate vicinity of said faces and having two open ends so that a part of the body may be maintained against at least one said abutment face and/or said corner and simultaneously against the external open end of said aperture or above it and be penetrated to the desire depth by the syringe needle in the advanced position of the latter.

According to a preferred embodiment, said stop member comprises a main portion and a removable additional portion enabling both intra-muscular and sub-cutaneous injections in the best conditions. The said main portion usually comprises two abutment faces intersecting so as to form a convex corner or angle at the level of or against which an articulation of a limb of the animal may be placed when said additional portion is removed, with both parts of the involved limb extending along and against said faces to enable an easy intra-muscular injection in one of said parts. The removable additional portion generally includes an arcuate face in extension of an abutment face of the main portion, when said additional portion is juxtaposed to said main portion, and thus defining with it a concave corner or angle at the level of or against which may be placed the head of the animal, while its neck is maintained against said abutment face to enable an easy sub-cutaneous injection in the neck area. When said main portion has two abutment faces intersecting so as to form a convex angle, one of said faces may be used for removably securing the additional portion onto the main portion.

According to the invention, the above stop member or main portion thereof may be provided with an auxiliary portion, integral with said stop member or rigidly secured thereto, said portion being juxtaposed to an abutment face of said stop member and said portion having a plane or spout-shaped external elongated face which is slightly inclined to the external surface of the retention plate, said elongated having one end substantially on a level with and in the immediate vicinity of the external open end of the aforesaid aperture of the retention plate. Thus, the neck of the animal may be placed on said elongated face and more easily fixed in position, in cooperation with the abutment face (or faces) of said stop member and possibly with a concave corner thereof.

The syringe body comprises a stop-forming part against which the piston abuts at the end of its backward stroke, thus enabling a highly accurate dosing to be obtained, the dosing accuracy being of at least 1%.

According to a preferred form of embodiment of the injection device of the invention, the syringe advance and withdrawal means comprise a motor secured to a stationary support comprising a preferably tubular portion in which slides or is guided the syringe body, the said motor imparting a rectilinear motion, controlled in amplitude and pre-determined in/stroke length, to a movable assembly connected only to the piston rod; otherwise stated, the syringe can be advanced only through the medium of the piston rod. The displacement of the said movable assembly is advantageously so performed as to first ensure a combined displacement of the syringe and its piston, and then, owing to the presence of a suitable stationary stop limiting the said combined displacement, a displacement of only the piston in order to carry out the injection.

Of course, use can be made, without departing from the scope of the invention, of a motor of any type, in particular an electric motor or a fluid-pressure motor, for example a compressed-air-motor.

Various types of stops are used to control each stage of the advance or the withdrawal of the said movable assembly, while suitable return springs are used, on the one hand, to return the movable assembly to its position of rest (withdrawn or rearward position) and, on the other hand, to return the syringe to its position of rest together with the piston in its "upper" position with respect to the syringe body.

According to one another feature of the invention, the said injection device comprises a control spring, the progressive compression of which, during a second portion of the stroke of the said movable assembly (displacement of the piston without displacement of the syringe body), enables a slackening of the displacement of the piston with respect to the syringe body, towards the end of displacement, the said spring being so arranged as to be loaded by the said motor.

Of course, the advance and the withdrawing of the syringe at each injection may be obtained either by moving the syringe body, the retention means remaining at a given stationary location or by displacing the said retention means with respect to said syringe body and needle which remain at a stationary location, the only movable part of said syringe being then the syringe piston.

BRIEF DESCRIPTION OF THE DRAWINGS

Other features and advantages of the present invention will appear from the following description made with reference to the appended drawings given solely by way of example and wherein.

DETAILED DESCRIPTION OF THE INVENTION

Figure 1:
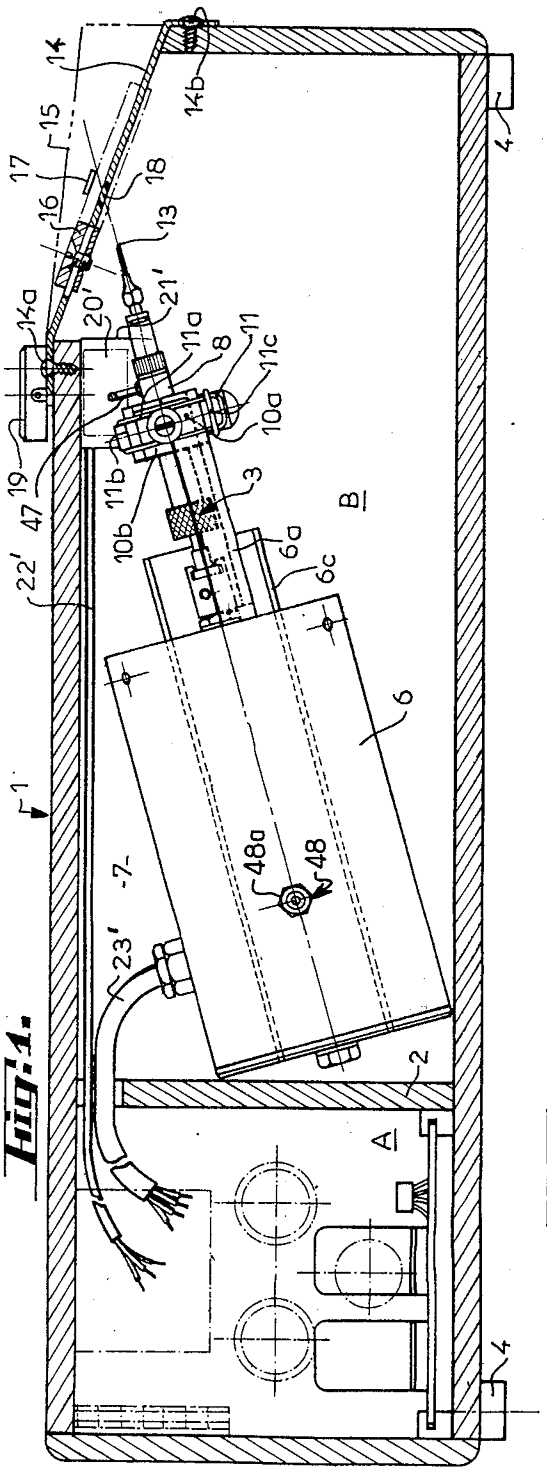
FIG. 1 is a longitudinal vertical cross-sectional view of an injection device provided with its casing according to a preferred form of embodiment of the invention, the said device being usuable in particular for the vaccination of chicks.
Figure 2:
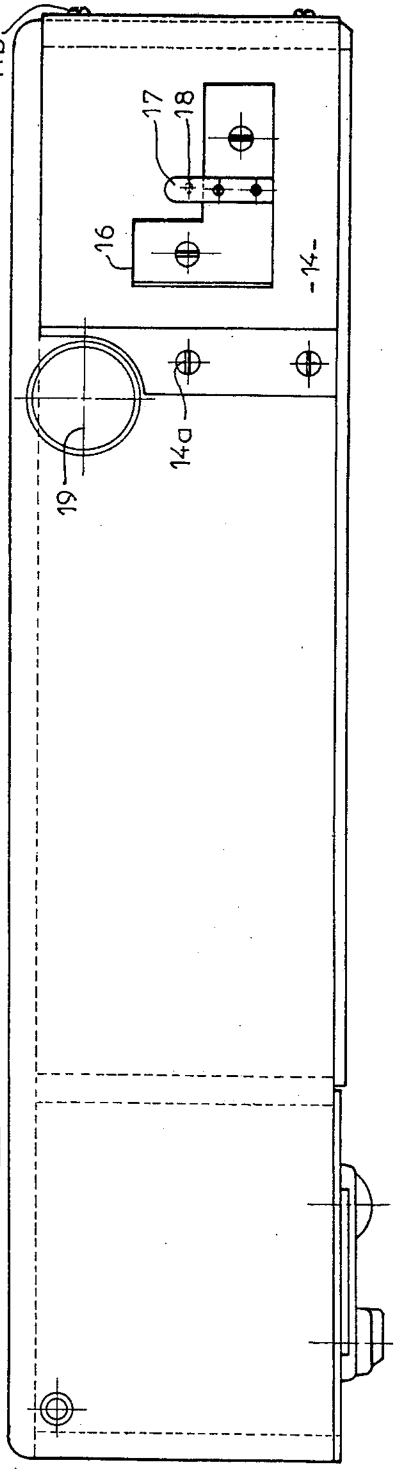
FIG. 2 is a top view of the same device.

The injection device of FIGS. 1 and 2 comprises a casing 1 resting or instance upon a table through the medium of stuck rubber-legs 4, the said casing comprising a partition 2 defining a section A containing the electronic control assembly and a section B containing the syringe 3 and an electric motor, the housing 6 of which is fixed to the side wall 7 of the casing 1 and serves as a support for the internal members of the motor and, through the medium of a semi-tubular extension 6*a* of the said housing, for the syringe 3, the body 8 of which can slide in two half-bearings (the lower one, 9*a*, of which appears in FIG. 3*b*), the said lower and upper half-bearings being retained by the end 10*a* of the semi-tubular extension 6*a* and by an upper half-sleeve 10*b* which is maintained applied against the end 10*a* by fixing means 11 comprising spring straps such as 11*a*, mounted on a hinge member 11*b* and maintained locked by means of a manually unlockable fastening member 11*c*, thus enabling the syringe to be rapidly mounted in or removed from the device; the syringe body 8 is provided with a lateral injection-liquid supply tubulure 47.

The fixing of the housing 6 in the wall 7 is performed by locking means 48 comprising a nut 48*a* tightened on the projecting threaded portion, at the end of the casing 1, of a rod 6*b* solid with the housing 6, the passage of the said rod through the wall 7 being allowed by a slit provided in the said wall and arranged in the direction of the common axis of the motor and the syringe 8, thus enabling, owing to suitable guide means 6*c*, the assembly formed of the housing 6, its extension 6*a*, the motor, the syringe 3 and its needle 13 to be displaced along the said axis. An oblique peripheral wall of the casing 1 constitutes a retention plate 14 which is screwed on the adjacent peripheral walls of said casing by means of screws such as 14*a* and 14*b*, so that the said plate is readily interchangeable and can be replaced by another plate somewhat different in profile, such as, for example, the one shown by the discontinuous line 15, thus enabling the injection angle to be modified. On the said retention plate is secured (screwed) a right-angled abutment or stop member 16 having two abutment faces which form between them an angle of 90° and carrying a stud 17 opposite and at a certain distance from the aperture 18 provided in the plate 14 and coinciding with the axis of the needle 13, which, when the device is in its position of rest, has its upper end substantially in proximity to the said aperture or just behind the latter without reaching the external surface of the plate 14. It is thus possible to accurately fix the injection region on the animal by maintaining it at a given location of the retention plate by using the abutment means 16 and 17 which, in the example illustrated, have a suitable structure enabling the articulation of the foot of the chick to be retained in place between the member 16 and the stud 17, the end of the foot being raised against one of said abutment faces and the leg being retained against the other abutment face under the stud 17 opposite the aperture 18, while the body of the animal is held by the operator with one hand and the raised foot with the other hand.

The injection may be, for example, intra-muscular or sub-cutaneous.

The structure and dimensions of the aperture are advantageously so selected as to ensure a certain muscular or cutaneous sinking in order to avoid any slip-away (by using an aperture which is sufficiently large and oval in shape owing to the obliquity of the needle with respect to the retention plate, the angle between the needle axis and the external surface of said plate being usually between 15° and 40°).

Individual control of the various injections is obtained by the operator by pressing his finger on a push-member 19 as soon as the animal is in place, the push-member being connected, through the medium of a relay 20' located in an insulating casing 21' and of wires 22', to the electronic control assembly contained in the section A and which starts the electric motor to which it is connected by the wires 23'.

According to a modified form of embodiment, such as that illustrated in FIGS. 4 to 7, each injection can be controlled by the actuation of a suitable contact caused by the putting in place of a limb or other part of the body of the chick or, if more safety is desired, the use of two types of contacts can be combined in order that the injection be controlled only when both contacts are actuated.

The structure of the injection syringe and that of the actuating means enabling the various phases of the injection process to be carried out will now be described with reference to FIGS. 3*a* and 3*b*. In these Figures are seen the housing 6 of the motor, its semi-tubular extension 6*a* and the syringe 3, the piston 20 and rod 21 of which are shown in addition to its body 8. The rod 21 is connected, through the medium of the syringe head 22, to a movable assembly 23 comprising the rod 23*a*, the rod head 24, the stud 25 whose ends are supported by the semi-tubular extension 6*a*, and the rear extension 26 of the said rod. The syringe body 8 is extended by a ring 27 screwed on the end of said body and provided with an internal shoulder 28 bearing upon a stop-forming part 29 provided with a flange 29*a* abutting against the end of the body 8, so that the external annular shoulder 30 formed by the said stop-forming part is retained between the two portions 8 and 27, so that the stop-forming part 29 is solid with the syringe body 8 and its front face 29*b* is in a pre-determined and very accurate position which constitutes a stop means for the piston 20 at the end of its rearward stroke; a return spring 31 of the piston bears, on the one hand, upon the syringe head 22 solid with the piston rod 21 and, on the other hand, upon an internal annular shoulder 32 of the said part 29. On the other hand, the front internal wall of the syringe body constitutes an abutment means for the piston at the end of its forward stroke. Under such conditions, the injected dose is highly accurate owing to the accuracy of the length of the piston stroke.

Figure 3A:
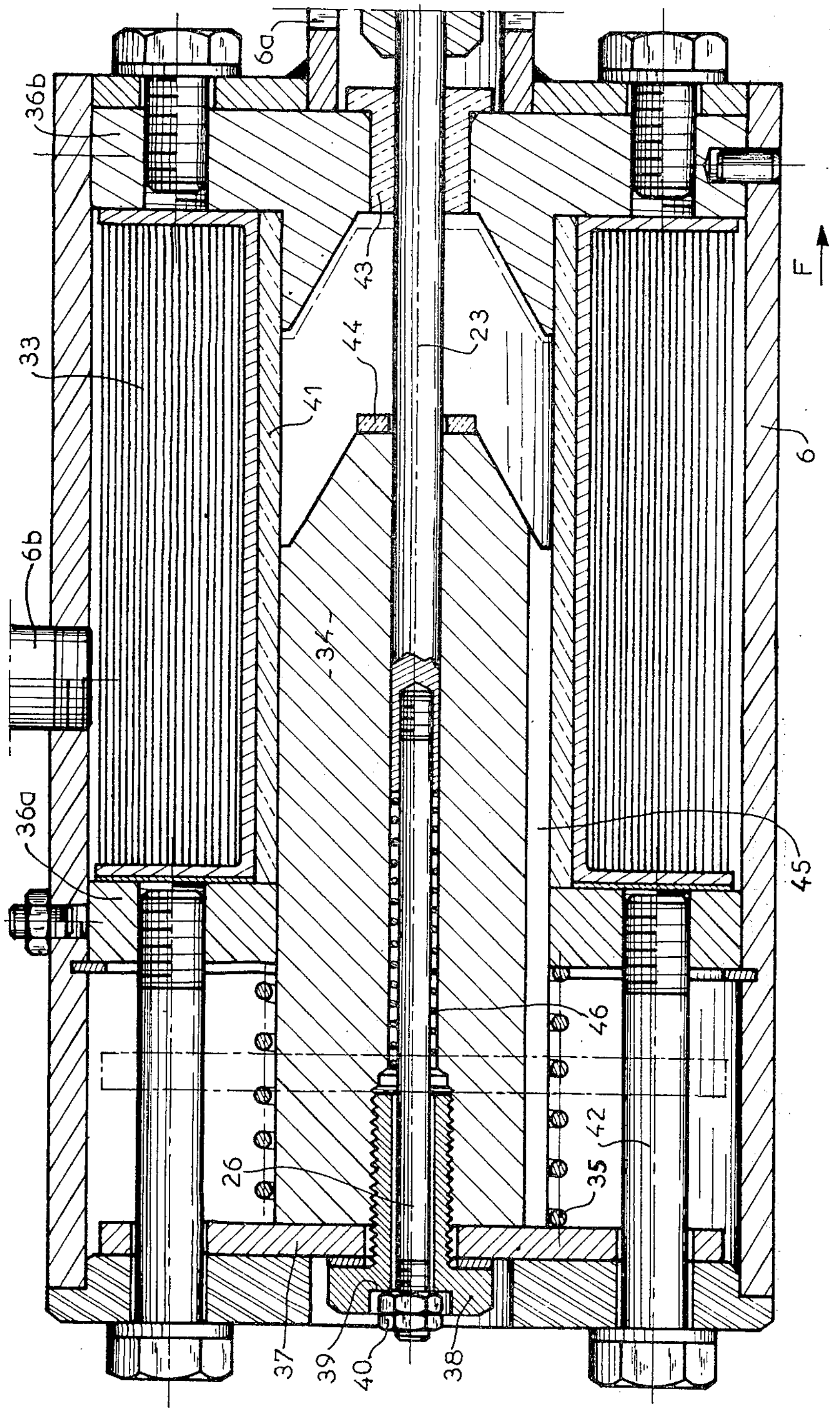
FIGS. 3*a* and 3*b* are axial sectional views of the motor, the injection syringe and the support of the said motor and syringe, in the withdrawn position of the syringe (position of rest).

Referring now more particularly to FIG. 3*a*, it is seen that the said electric motor comprises essentially a winding 33 supplied by a cable 23' (FIG. 1) and forming an electromagnet, a magnetic core forming a drive piston 34 capable of being actuated by the said electromagnet so as to perform a rectilinear motion over a predetermined length under the action of the electromagnetic forces in the direction of the arrow F (forward motion) and a return spring 35 of the said drive piston, subsequent to the interruption of the excitation of the electromagnet 33, the said return spring 35 bearing, on the one hand, upon the plate 36*a* and, on the other hand, upon the piston ring 37 secured to the drive piston 34 by a hollow screw 38 provided with an internal annular recess 39 which constitutes an adjustable stop for the terminal part of the movable assembly, i.e. the rear end of the rear extension 26 of the rod 23*a* such terminal part protruding from the rear end, namely the screw 38 and the piston ring 37, of the drive piston 34; such a stop is adjustable owing to the nuts 40 provided on the threaded end of the said extension. It is also observed that the drive piston 34 is guided by a guide tube 41 as well as screws such as 42 passing through the piston ring 37; on the other hand, the front end of the drive piston 34 is capable of abutting against the rod bearing 43 and the front plate 36*b*, a ring 44 being provided at the said front end; the total stroke of the said drive piston the rear end plate of housing 6 forms a stop limiting the rearward motion of the drive piston 34 is equal to the total stroke of the movable assembly 23, i.e. to the sum of the penetration stroke (syringe body stroke) and the injection stroke (displacement of the syringe piston alone). Furthermore, an intermediate spring 46 bears, on the one hand, upon the rod 23*a* and, on the other hand, upon the hollow screw 38.

In addition, a slot 45 is provided to balance the pressures on either side of the drive piston 34 during its displacement.

The injection devices of FIGS. 1 to 3*b* operates as follows.

Figure 3B:
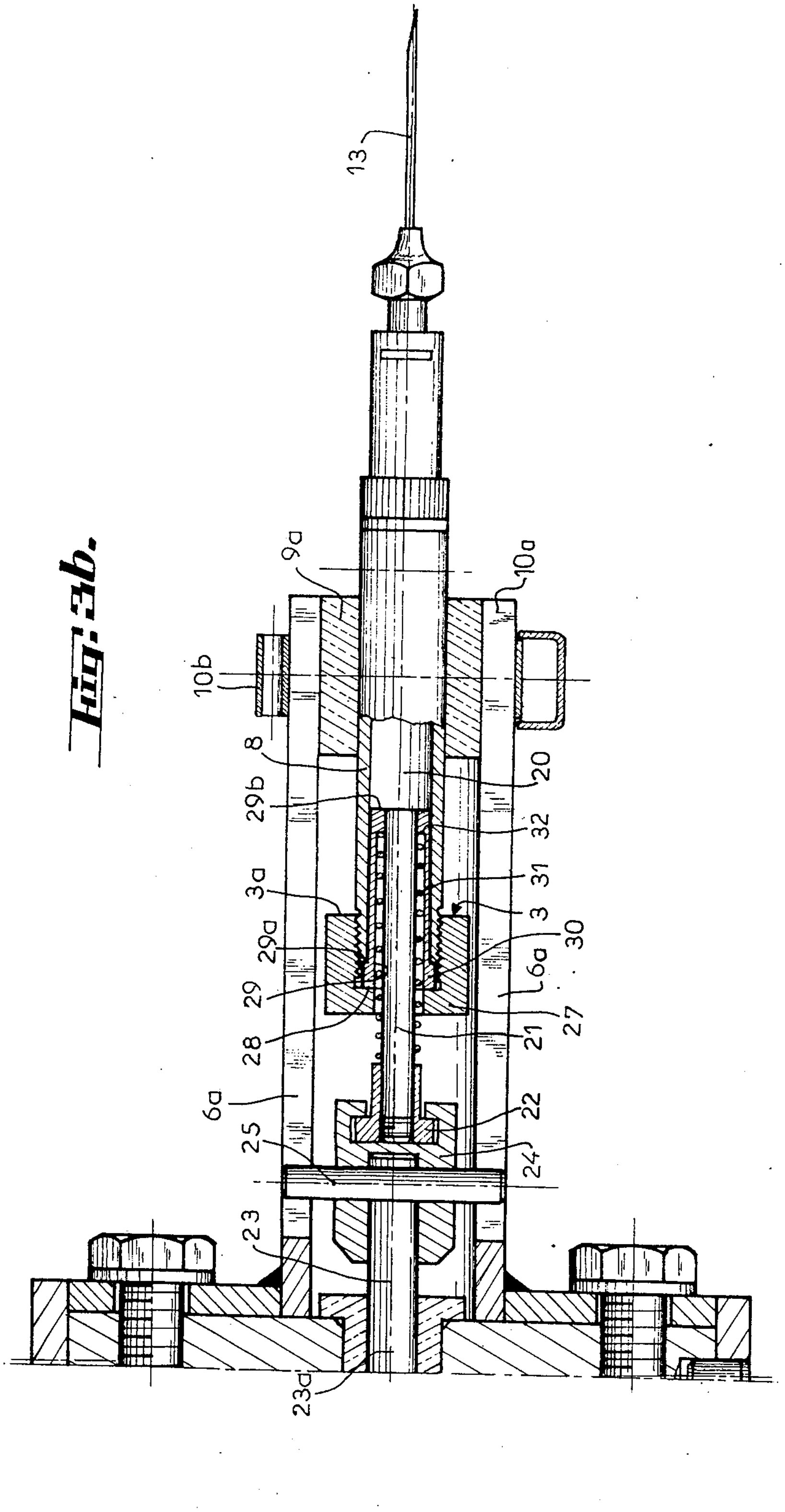

The animal to be treated is first placed, in the manner already described above, on the retention plate 14 (FIGS. 1 and 2), the device then being in the state shown in FIGS. 1, 3*a* and 3*b*. The operator then presses on the push-member 19, thus causing the electromagnet 33 to be excited during a predetermined period. From the position shown in FIG. 3*a* the drive piston 34 moves with the movable assembly 23 in the direction of the arrow F until it reaches a position where it abuts against the rod bearing 43; but before it reaches this position (i.e. at about 4/5 of its stroke in the example considered), the front face 3*a* of the knurled ring 27 reaches a position where it abuts against the rear face of the semi-bearings, such as 9*a*, thus stopping the forward displacement of the body 8 of the injector. At this moment, the needle 13 has already projected outwardly from the casing and has penetrated to a desired depth into the body of the animal, while the displacement of the drive piston 34 continues; the spring 46 is then progressively compressed, for a high resistance to the advance of the movable assembly 23 and the piston 20 is now offered by the injection liquid, while the liquid previously introduced into the syringe is progressively injected under the action of the displacement of piston 20; at the same time, the return spring 31, the calibrated force of which is smaller than that of the rod spring 46, is progressively compressed; due to the progressive compression of spring 46, the forward displacement of piston 20 with respect to the syringe body is slackened towards the end of said displacement, thus enabling the utilization of all the dosage without shock of the piston against the syringe body.

As soon as all the liquid of the syringe is injected, i.e. as soon as the piston 20 of the syringe reaches the end of its forward displacement, the feeding of the electromagnet 33 is stopped, so that the drive piston 34, under the action of the return spring 35, is moved back towards its initial position, i.e. that of FIG. 3*a*, while springs 46 and 31 loosen; during the displacement of drive piston 34, the nuts 40 bear again upon the internal annular recess 39, so that the movable assembly 23 and the piston 20 are driven to their rearward positions at the same time as the drive piston. A further dose of injection liquid is introduced into the syringe 3 under the action of a sucking taking place in the lateral intake tubulure 47 during the injection. On the other hand during said backward movement of the movable assembly, the piston 20 comes again in abutment against the face 29*b* of the stop-forming part 29 of the syringe body so that the latter is moved back to its initial position. A new cycle can begin, the state of the system being performed after the following animal is placed on the retention table and the push-member 19 is actuated.

Such a device enables about at least 2000 chicks to be vaccinated per hour, while at the same time ensuring a dosing accuracy on the order of 1/100 and exact location of the point of injection, as well as an accurate injection depth.

Figure 6:
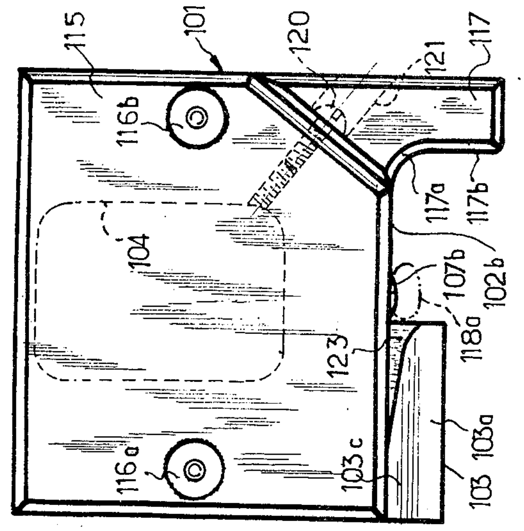
FIG. 6 is a top view of the stop member of FIG. 4, said member being provided with its cover and with a removable additional portion more specifically intented to use the invention device for sub-cutaneous injections.
Figure 5:
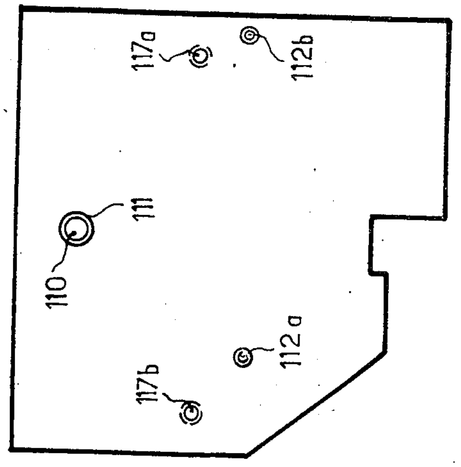
FIG. 5 is a bottom view of said stop member, with its push-button removed.
Figure 4:
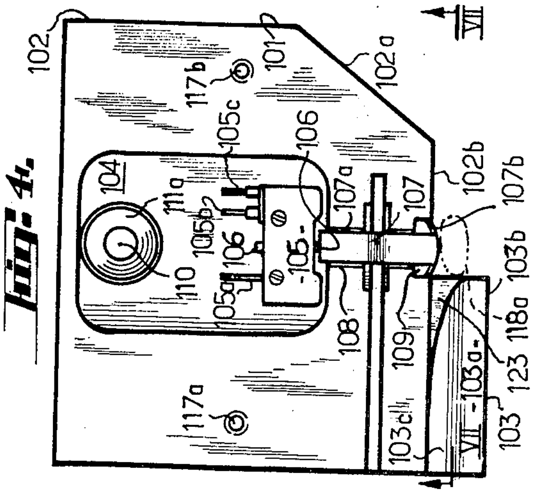
FIG. 4 is a top view of the stop member of the retention means of an injection device to another preferred form of embodiment of the invention, particularly adapted to the vaccination of chicks, the cover of said stop member having been removed to show the internal structure of said stop member.

The stop member 101 of FIGS. 4, 5 and 6 consists of a thick plate 102, for example made of light alloy, having a square or rectangular shape, having a plane main abutmennt face 102*a* and a plade first auxiliary abutment face 102*b* (forming an obtuse angle with said main abutment face), onto at least one of which may be immobilized a limb or other part of an animal the said abutment faces intersecting to form a convex corner or angle; said plate 102 comprises an auxiliary portion 103 integral therewith, the elongated external surface 103*a* of said portion being plane towards its external edge 103*b* and joining the plane abutment face 102*b*, along a fraction of the length of the latter, by an accurate surface portion 103*c*.

As it may be seen in FIG. 4, said plate 102 comprises an internal cavity 104 which contains an electrical micro-switch 105 including a movable element 106 likely to be actuated by the push-button 107 which is U-shaped, the central branch 7*a* of said U being located in a groove 108 of the plate 102, while one of the lateral branches of said U is in contact with the movable element 106, the other branch, referenced 107*b* being less or more introduced in the cavity 109 open over the whole height of the abutment face 102*b* (see also FIG. 6); at rest, said branch 107*b* slightly protrudes from said face 102*b* and is pushed towards the bottom of cavity 109, while pushing in turn the movable element 106 and thereby actuating micro-switch 105, when a limb or any other part of an animal body is applied against the abutment face 102*b* by the operator. Thus, the starting of each injection operation is immediately obtained when the animal is put in place on the retention plate. It is seen that cavity 104 comprises an aperture 110, provided with a tubular element 111 made of electrically insulating material, said tubular element having a protruding portion 111*a* at its end located inside the cavity 104, which enables to maintain in place said tubular element; aperture 110 allows the passage of an electric cable, the leads of which are connected to terminals 105*a*, 105*b* and/or 105*c* of micro-switch 105 so as to permit the control of each injection operation by means of conventional circuits pursuant to the depression of the push-button 107.

The position of the external open end of the aperture of the retention plate (said plate being shown in FIG. 7) is represented by the dotted line referenced 118*a*.

FIG. 5 shows the internal or lower face of the stop member 101, namely the face thereof which is normally applied against the retention plate. The fixing of said stop member on said plate is for example obtained by means of threaded rod 112*a* and 112*b* which may be engaged by serrated or embossed nuts such as those represented by reference numbers 113*a* and 113*b* in FIG. 7.

In FIG. 6, the stop member 101 is provided with its cover 115 having a bevelled peripheral edge and maintained by screws 116*a* and 116*b* equipped with serrated or knurled heads and of which the threaded rods are screwed in the threaded bores, respectively 117*a* and 117*b*, of plate 2 (see FIGS. 4 and 5).

FIG. 6 also shows that the stop member 101 is provided with a removable additional portion 117 which is rigidly secured to plate 102, along the face 102*a* of the latter, by means of a screw 120 the head of which is located in duct 21 and rests on an inner peripheral shoulder of said duct, both said screw and duct being represented in dotted lines; the thickness of said portion 117 is suubstantially the same as that of the main portion of stop member 101, i.e. plate 102, so that the continuity is ensured from the abutment face 102*b* of plate 2 to the short abutment plane face 117*b* of the removable portion 117 by the intermediary of the arcuate face 117*a* of said portion which thus forms a concave corner or angle.

Figure 7:
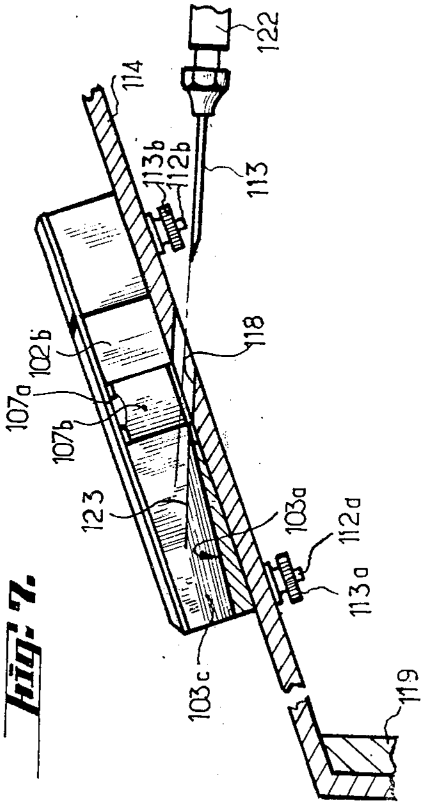
FIG. 7 is a vertical cross-sectional views of the retention means and cooperating injection needle of the injection device of FIGS. 4 to 6, along line VII—VII of FIG. 4, the remaining part of said injection device having for instance the structure of the corresponding part of the injection device of FIGS. 1 to 3*a*–3*b*.

Referring now to FIG. 7, it is seen how stop member 101 of FIGS. 4 to 7 is disposed with respect to the retention plate 114, the aperture 118 thereof, the casing 119 onto which is mounted said plate, preferably in a removable manner, and syringe 22 with its needle 113 adapted to pass through aperture 118 in the same conditions as in the embodiment of FIGS. 1 to 3*b*. It must be noted that the incurved surface portion 103*c* of the auxiliary portion 103 is slightly bevelled in its lower portion, the bevelling plane being referenced 123 in FIGS. 4, 6 and 7. Said Figure also shows that surface 103*a* is slightly inclined to the external surface of the retention plate 114.

The device of FIGS. 4 through 7 is used in the following manner, for example to vaccinate chickens:

a. sub-cutaneous injection of the vaccine

The stop member 101 having been mounted on the retention plate 114, as shown in FIG. 7, and its removable additional portion 117 having been secured to said stop member 101, as shown in FIG. 6, the chick is taken by the hand of the operator which places the head of the animal against the arcuated edge 117*a* in such a manner that the neck be maintained above the aperture 18 and the auxiliary portion 103, more specifically the surface 103*a*, the body of the animal being maintained in an elongated state; the neck may be maintained in position by only one finger while the other fingers of the same hand maintain the remaining part of the said body; said positioning of the chicken actuates the push-button 107 which controls the injection operation; the mere opening of the hand of the operator releases the chicken which then slides on the inclined plane formed by the retention plate to fall down in a suitable reception vessel, not shown.

b. intra-muscular injection of the vaccine

In this case, the removable additional portion 117 is separated from the plate 112, so that the stop member which is then used is that shownin FIG. 4, the dismounting of portion 117 being carried out without having to dismount the plate 112 secured on the retention plate 114. The chicken to be vaccinated is caught by its body with one hand of the operator, while the other hand catches the end of the left foot and applicates the articulation angle of said foot against the convex corner of the plate 102, at the intersection of the abutment faces 102*a* and 102*b*, the foot extending along the face 102*a* whereas the leg extends along and against the face 102*b* and against the external open end of aperture 118, the application of said leg against said face 102*b* causing the depression of the push-button 107 and the command of a single injection step; the chicken is released by opening the hand when the injection syringe has come back to its rearward or withdrawn position. Thus, the shape and structure of the retention means ensure a safe and easy positioning of the chicken starting from simple anatomic marks or references and even non professional or unexperienced persons may become very skilled operators within a short period of time; the efficiency of the vaccinations is increased and considerably improved vaccination rates may be obtained. Further, the passage from the most suitable structure for the sub-cutaneous vaccination to the most adequate one for the intra-muscular vaccination may be as short as about ten seconds.

Of course, the invention is by no means limited to the form of embodiment described and illustrated, which has been given by way of example only. In particular, it comprises all the means constituting technical equivalents to the means described as well as their combinations, should the latter be carried out according to the spirit of the invention.

What is claimed is:

1. Automatic injection device comprising a casing formed by a plurality of peripheral walls, syringe support means rigidly mounted in said casing, an injection syringe located within said casing and including a syringe body slidably mounted on said syringe support means and provided with a lateral injection-liquid supply tubulure, a syringe piston provided with a piston rod and adapted to slide in said syringe body, and an injection needle rigidly secured to said syringe body, retention means for immobilizing a part of an animal to be treated, said retention means comprising at least one retention plate formed by one of said peripheral walls and having an external surface which is a part of the outer surface of the casing, and at least one stop member rigidly secured to said retention plate and extending outside of said casing, parallel to and in contact with a part of the external surface of said retention plate, said stop member having a plane elongated main abuutment face and at least one auxiliary abutment face, each face being substantially perpendicular to said retention plate and being angularly related one to the other, first displacement means for advancing and withdrawing the syringe body, at each injection, with respect to said retention means, and piston displacement means for displacing said piston with respect to said syringe body, said retention plate being provided with an aperture which opens at a point located close to said main abutment face and in the vicinity of said auxiliary abutment face, on a part of the external surface of said retention plate which is clear of said stop member, through which aperture said injection needle may be displaced with respect to said retention plate by said first displacement means so as to protrude outwardly beyond the external surface of the retention plate in the advanced position of the syringe body thereby enabling injection, said injection needle being inwardly disposed relative to said external surface in the withdrawn position of the syringe body.

2. Injection device according to claim 1, wherein said retetion plate is removably and interchangeably mounted on adjacent peripheral walls of said casing.

3. Injection device according to claim 1, wherein said auxiliary abutment face is plane and forms an obtuse angle with main abutment face.

4. Injection device according to claim 1, wherein said auxiliary abutment face comprises a concave part and a plane part, said concave part being between said plane part and said main abutment face and being in extension of both said plane part and said main abutment face.

5. Injection device according to claim 4, wherein said stop member comprises an auxiliary portion along said main abutment face and having an elongated top face which is slightly inclined to the external surface of the retention plate and which has one end substantially on a level with and in the immediate vicinity of said aperture.

6. Injection device according to claim 1, wherein said stop member comprises a main portion having said main abutment face and said auxiliary abutment face, comprising a planar face, forming an obtuse angle with said plane main abutment face, and a removable additional portion having a concave part and a plane part predeterminately related to said main portion and to said auxiliary abutment face, said concave part being between said planar face of the auxiliary abutment face and said main abutment face and forming an extension of both said planar face and said main abutment face.

7. Injection device according to claim 1, wherein said first displacement means and piston displacement means comprise an electric motor secured to said casing and having a housing, said support means comprise said housing and a tubular extension thereof extending parallel to said piston rod and in which said syringe body is slidingly mounted, said electric motor being adapted to reciprocate a movable assembly, rigidly connected to said syringe piston rod, in a rectilinear reciprocating motion parallel to said syringe piston rod and defining a forward stroke and a rearward stroke for said movable assembly and said syringe piston and piston rod.

8. Injection device according to claim 7, wherein said support means comprise a stop limiting the forward stroke of the syringe body, said forward stroke corresponding to a first portion of the forward stroke of said movable assembly, so that the forward displacement of the piston with respect to said syringe body takes place, while said syringe body is maintained in said advanced position by said stop, in a second portion of the stroke of said movable assembly.

9. Injection device according to claim 7, wherein said electric motor is provided with a magnetic core slidingly movable parallel to the piston rod of said syringe and actuated in forward motion when said motor is energized, for carrying out the forward stroke of said movable assembly, and with a return spring which produces a rearward motion, of amplitude equal to that of said forward motion, of said magnetic core when said motor is de-energized.

10. Injection device according to claim 9, wherein said magnetic core comprises an axial duct in which is located a rear portion of said movable assembly and an intermediate heliciodal spring is placed in said duct between an internal shoulder of said magnetic core and a shoulder of the rear portion of said movable assembly, said movable assembly and said magnetic core being solidarily displaced in a first portion of the forward motion of said magnetic core while relative displacement of said magnetic core with respect to said movable assembly with progressive compression of said intermediate spring is enabled in a second portion of the forward motion of said magnetic core, after said syringe body has come in abutment with said stop.

11. Injection device according to claim 10, wherein the housing of said motor comprises first stop means limiting the forward motion of said magnetic core by abutment of the front end of said magnetic core with said first stop means and second stop means limiting the rearward motion of said magnetic core by abutment of a part of the rear end of said magnetic core with said second stop means, another part of said rear end forming a contact surface resting during the rearward motion of said magnetic core against a contact front face of a terminal part of said movable assembly which is adapted to permanently protrude from said rear end.

12. Injection device according to claim 11, wherein said casing comprises guide means parallel to said piston rod, said support means being slidingly mounted in said guide means, locking means being provided to secure sais support means at a given, variable position with respect to said casing.

13. Injection device according to claim 1, comprising controlling means for controlling, at each injection, said displacement means and said piston displacement means, through actuation of a starting member operated at the beginning of each injection operation.

14. Injection device according to claim 13, wherein said starting member is a push-button located in a recess provided in said abutment face and slightly protruding on said abutment face, enabling said push-button to be actuated by the positioning of an animal to be treated against said abutment face.

15. Injection device according to claim 14, wherein said injection syringe comprises a piston return spring for returning the piston to its rearward position, said piston return spring bearing at its front end upon said syringe body and at its rear end upon an enlarged portion of the piston rod.

16. Injection device according to claim 1 wherein the angle between said external surface of said retention plate and said piston rod direction is ranging from 15° to 40°.

* * * * *